US008152760B2

(12) United States Patent
Boatman

(10) Patent No.: US 8,152,760 B2
(45) Date of Patent: Apr. 10, 2012

(54) MEDICAL BALLOON HAVING A RESISTANCE TO CIRCUMFERENTIAL TEARING AND METHOD OF PRODUCING THE BALLOON

(75) Inventor: Scott E. Boatman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/207,928

(22) Filed: Sep. 10, 2008

(65) Prior Publication Data

US 2010/0063442 A1    Mar. 11, 2010

(51) Int. Cl.
*A61M 31/00* (2006.01)
(52) U.S. Cl. .................................. 604/103.06
(58) Field of Classification Search ............... 604/96.01
See application file for complete search history.

(56) References Cited

U.S. PATENT DOCUMENTS

| 3,211,152 A | 10/1965 | Stern |
| 5,038,777 A | 8/1991 | Dunn |
| 5,049,131 A | 9/1991 | Deuss |
| 5,318,587 A | 6/1994 | Davey |
| 5,391,148 A | 2/1995 | Bonis |
| 5,458,572 A | 10/1995 | Campbell et al. |
| 5,478,320 A | 12/1995 | Trotta |
| 5,868,707 A | 2/1999 | Williams et al. |
| 6,129,706 A | 10/2000 | Janacek |
| 6,355,013 B1 | 3/2002 | van Muiden |
| 6,544,224 B1 | 4/2003 | Steese-Bradley |
| 7,300,448 B2 | 11/2007 | Criscuolo et al. |
| 2007/0073328 A1 | 3/2007 | Kennedy, II |
| 2009/0299450 A1* | 12/2009 | Johnson et al. ............. 623/1.11 |

FOREIGN PATENT DOCUMENTS

GB    1327858    8/1973

* cited by examiner

*Primary Examiner* — Nicholas Lucchesi
*Assistant Examiner* — Jason Flick
(74) *Attorney, Agent, or Firm* — Brinks Hofer Gilson & Lione

(57) ABSTRACT

A medical balloon having a resistance to circumferential tearing comprises a substantially cylindrical portion disposed between first and second tapered portions that have a decreasing cross-sectional area along a length thereof away from the cylindrical portion. The substantially cylindrical portion includes first and second end portions and a midsection disposed therebetween. The midsection includes a first region having a first resistance to tearing and a second region having a second lower resistance to tearing, where the second region extends about only a portion of the circumference of the cylindrical portion and does not extend beyond the midsection.

8 Claims, 3 Drawing Sheets

610 Providing a medical balloon comprising a substantially cylindrical portion having first and second end portions and a midsection disposed therebetween

620 Weakening a localized region of the midsection, the localized region extending about only a portion of a circumference of the cylindrical portion and not extending beyond the midsection

Figure 6

MEDICAL BALLOON HAVING A RESISTANCE TO CIRCUMFERENTIAL TEARING AND METHOD OF PRODUCING THE BALLOON

TECHNICAL FIELD

The present disclosure relates generally to medical devices and more particularly to medical balloons.

BACKGROUND

Angioplasty balloons are widely used to dilate stenosed regions of blood vessels. Typical practice is to increase the inflation pressure in the balloon at the stenosed region until the vessel yields and optimal blood flow has been restored. In some instances, however, the inflation pressure may be increased to such a degree that the balloon bursts. If the balloon fails or tears longitudinally and remains in one piece, the burst may not be particularly problematic. If, on the other hand, a longitudinal tear propagates to the taper or neck of the balloon and changes direction, the balloon may experience a "radial burst" and fragment into two or more pieces. The resulting balloon fragments may be embolized and remain in the vessel even after the balloon catheter has been withdrawn, potentially threatening the health of the patient.

BRIEF SUMMARY

A medical balloon having a resistance to circumferential tearing and a method of making the medical balloon is described herein.

According to a first aspect, the medical balloon comprises a substantially cylindrical portion disposed between first and second tapered portions that have a decreasing cross-sectional area along a length thereof away from the cylindrical portion. The substantially cylindrical portion includes first and second end portions and a midsection disposed therebetween. The midsection includes a first region having a first resistance to tearing and a second region having a second resistance to tearing, where the second resistance to tearing is lower than the first resistance to tearing and also lower than a resistance to tearing of the first and second end portions. The second region extends about only a portion of the circumference of the cylindrical portion and does not extend beyond the midsection.

According to a second aspect, the medical balloon comprises a midsection disposed equidistant between first and second ends of the medical balloon and spanning no more than about 30% of a total length between the first and second ends. The midsection includes a weakened localized region not extending beyond the midsection.

The method of fabricating a medical balloon having a resistance to circumferential tears includes providing a medical balloon comprising a substantially cylindrical portion having first and second end portions and a midsection disposed therebetween, and weakening a localized region of the medical balloon in the midsection, the localized region extending about only a portion of a circumference of the cylindrical portion and not extending beyond the midsection.

BRIEF DESCRIPTION OF THE DRAWINGS

FIG. 6 is a flow chart showing steps of the method according to one aspect.

DETAILED DESCRIPTION

A medical balloon having a resistance to circumferential tearing is described herein. The medical balloon includes at least one weakened localized region in a midsection thereof, where the midsection is defined with respect to a longitudinal axis of the balloon. The weakened localized region is a small portion of the balloon that has a lower resistance to tearing than other portions of the balloon and thus acts as a failure initiation site at high inflation pressures. The inventor has recognized that if a failure occurs in the midsection of the balloon, it tends to propagate longitudinally and substantially dissipate its energy before it reaches one or both ends, where longitudinal tears otherwise tend to change direction and move circumferentially. By engineering the medical balloon to include such a weakened localized region in the midsection, circumferential tears that may result in the balloon's fragmenting into two or more pieces ("radial bursts") can be avoided.

Figure 1:
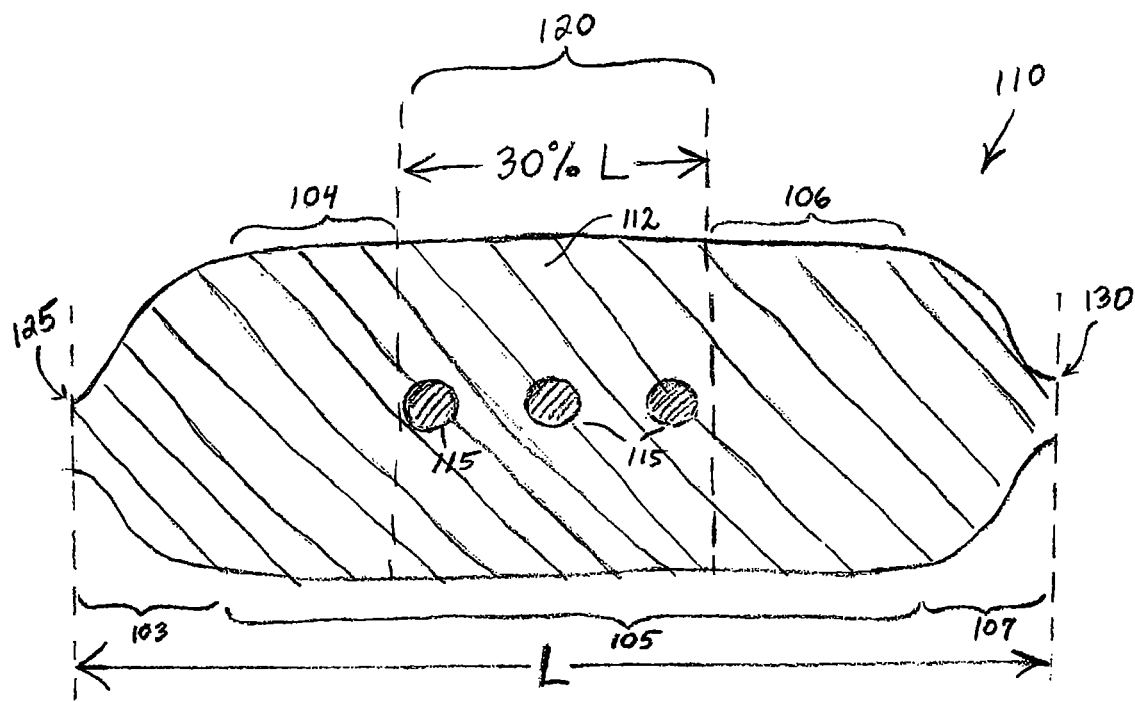
FIG. 1 is a schematic of a medical balloon including more than one weakened localized region in a midsection thereof.

Referring to the embodiment shown in FIG. 1, the medical balloon 110 includes a substantially cylindrical portion 105 disposed between first and second tapered portions 103,107. The first and second tapered portions 103,107 have a decreasing cross-sectional area along a length thereof away from the cylindrical portion 105. The decrease in the cross-sectional area may be linear or nonlinear. The substantially cylindrical portion 105 includes first and second end portions 104,106 and a midsection 120 disposed therebetween. The midsection 120 has a first region 112 having a first resistance to tearing and at least one second region 115 having a second resistance to tearing, where the second resistance is lower than the first resistance and also lower than a resistance to tearing of the first and second end portions 104,106. The first resistance to tearing may be the same as the resistance to tearing of the first and second end portions 104,106. The second region 115 extends about only a portion of a circumference of the substantially cylindrical portion 105 and does not extend beyond the midsection 120.

Figure 2:
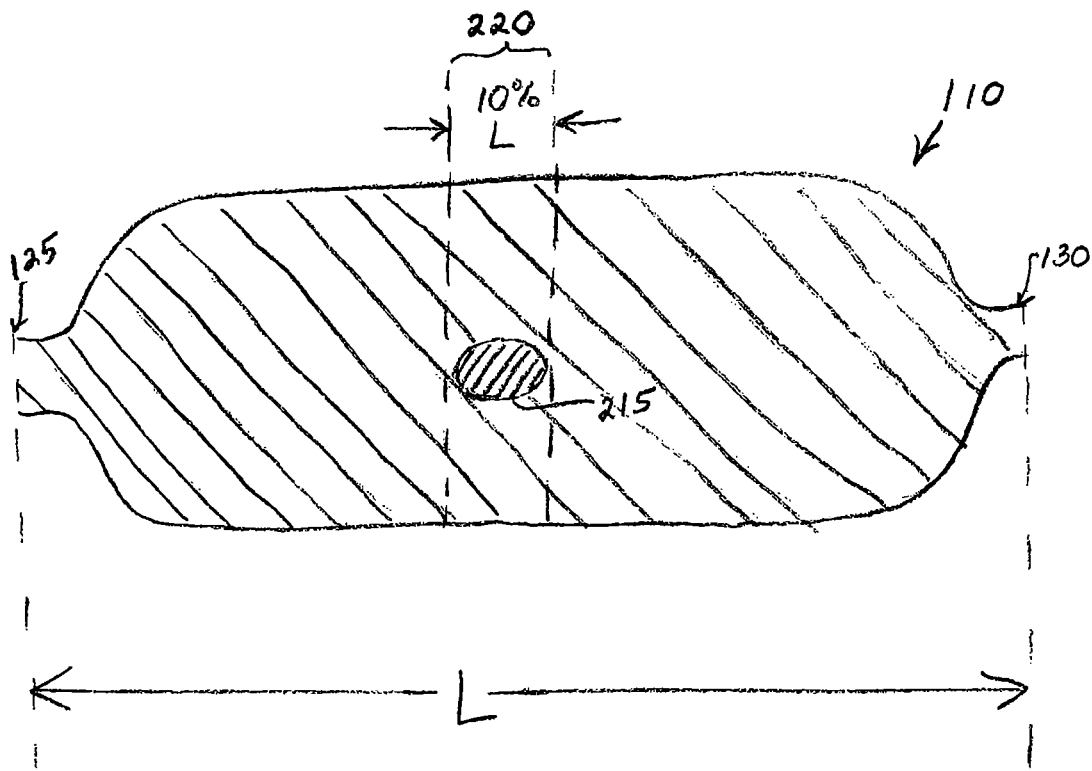
FIG. 2 is a schematic of a medical balloon including a weakened localized region in a midsection thereof.

The midsection 120 of the medical balloon 110 is disposed equidistant between first and second ends 125, 130 of the balloon 110 and preferably spans no more than about 30% of the total length L from the first end 125 to the second end 130, as shown in FIG. 1. The midsection 220 of the medical balloon 110 may also be defined as spanning no more than about 10% of the total length L, as shown in the embodiment of FIG. 2. Typically, medical balloons 110 have total lengths L ranging from about 10 mm to about 80 mm, although longer or shorter lengths are possible. The balloon 110 includes at least one weakened localized region 115, 215, and the region 115, 215 does not extend beyond the midsection 120, 220, as indicated in the figures.

Figure 3:
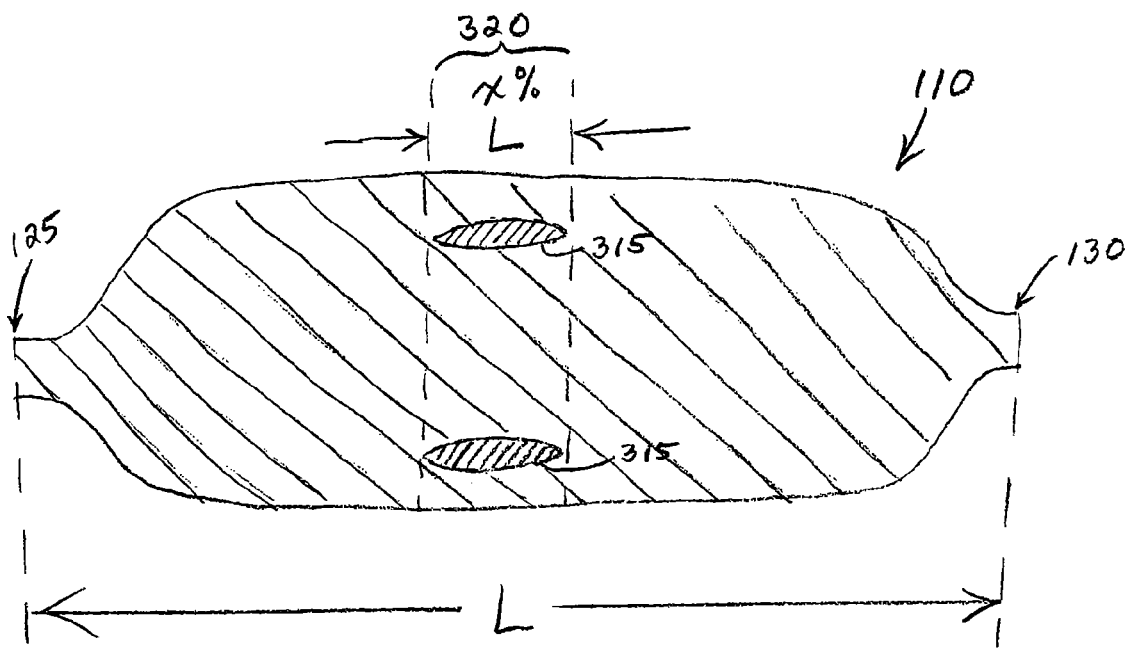
FIG. 3 is a schematic of a medical balloon including more than one weakened localized region in a midsection thereof.

The medical balloon 110 may include two or more weakened localized regions 115. FIG. 1 depicts three weakened localized regions 115 aligned longitudinally along the midsection 120 of the balloon 110. Other arrangements of weakened localized regions are also possible. For example, as shown in FIG. 3, the weakened localized regions 315 may be aligned or otherwise situated circumferentially about the balloon 110 within the midsection 320. In this exemplary figure, each weakened localized region 315 extends across the midsection 320 having an arbitrary length corresponding to x % of L, the total length of the balloon, where x may be, for example, about 1, 5, 15, 20, or 25.

Although the weakened localized regions may be circumferentially arranged, the one or more weakened localized regions do not extend about a substantial portion of the circumference of the medical balloon. If the weakened localized region spans more than a small portion of the balloon's circumference, the initial failure may propagate circumferentially instead of longitudinally, potentially causing a radial burst at the balloon's midsection. Preferably, the weakened localized region or regions span less than about 10% of the circumference. They may also span less than about 5% of the circumference.

The weakened localized region can have any shape. For example, the region 115, 215, 315 may be substantially circular (e.g., see FIG. 1) or oval (e.g., see FIG. 2) or have another regular shape (e.g., see FIG. 3), or it may be irregularly shaped.

According to one embodiment, the weakened localized region comprises a surface area of about 10 $mm^2$ or less. Preferably, the surface area of the weakened localized region is about 5 $mm^2$ or less. For an exemplary balloon of about 50 mm in length and 8 mm in inflated diameter, the total surface area of the balloon may be over 1350 $mm^2$. Accordingly, the surface area of the weakened localized region corresponds to only a small fraction of the total surface area of the balloon, generally less than about 1%, depending on the specific balloon dimensions. Where the medical balloon includes more than one weakened localized region, the regions may have in sum the above-described surface area.

The weakened localized region may extend from a surface of the balloon (e.g., the outer surface) partially through a thickness of the medical balloon. It is also contemplated that the weakened localized region may extend entirely through the thickness of the medical balloon. The weakened localized region may be visually distinguishable from other regions of the medical balloon by, for example, a difference in opacity or coloration of the region.

Typically the medical balloon including the weakened localized region is fabricated of a non-compliant or semi-compliant polymer such as, for example, polyethylene terephthalate (PET), nylon-12, or PEBAX. Compliant polymers may also be used, if desired. The weakened localized region may have a modified polymer structure (e.g., broken polymer chains or crosslinks).

Figure 4:
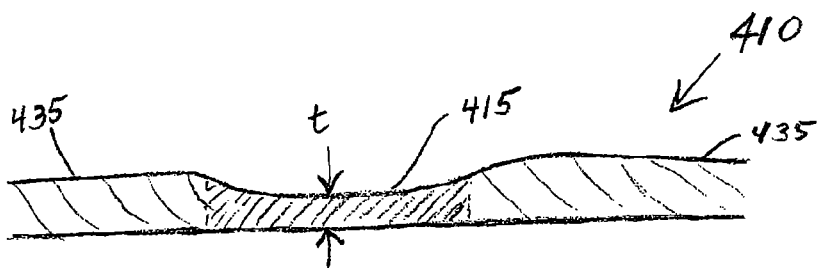
FIG. 4 is a cross-sectional schematic of a portion of a medical balloon including a weakened localized region.
Figure 5:
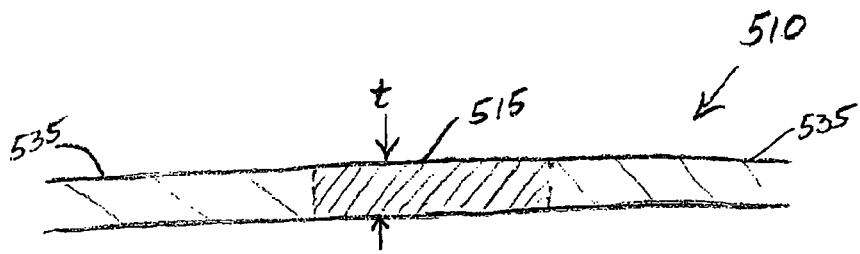
FIG. 5 is a cross-sectional schematic of a portion of a medical balloon including a weakened localized region.

Referring to FIG. 4, the weakened localized region 415 may also or alternatively have a reduced wall thickness t compared to other regions 435 of the medical balloon, as shown schematically in the cross-sectional view of a portion 410 of an exemplary medical balloon. Preferably, however, the polymer structure is modified while the wall thickness t of the weakened localized region 515 is substantially the same as that of other regions 535 of the medical balloon, as depicted in FIG. 5, which shows a cross-sectional view of a portion 510 of a second exemplary medical balloon. The modified polymer structure and/or reduced wall thickness may be obtained by thermal or physical processing of the balloon.

A method of fabricating a medical balloon having a resistance to circumferential tears is described below.

Referring to FIG. 6, the method includes providing 610 a medical balloon comprising a substantially cylindrical portion having first and second end portions and a midsection disposed therebetween, and weakening 620 a localized region of the midsection, the localized region extending about only a portion of a circumference of the cylindrical portion and not extending beyond the midsection.

The localized region of the midsection may be weakened by thermal and/or mechanical processing, and such processing may be applied to (1) the tubular preform from which the medical balloon is formed, or (2) to the medical balloon after forming from the preform. The preform may be a length of extruded polymer tubing of a predetermined diameter and wall thickness suitable for forming into a medical balloon by methods known in the art.

The localized region may be thermally processed to form the weakened localized region by heating the localized region to a temperature at or above the melt temperature or another characteristic temperature of the polymer. A radiofrequency heat source or another heating element (hot air, laser, resistance, etc.) that can provide focused or localized heating may be suitable for carrying out the thermal processing of the localized region.

For instance, a small resistance heating element may be used to locally heat a portion of the balloon or the tubular pre-form from which the balloon is formed. The element can be configured into the desired size and shape and brought close to or into contact with an inner or outer wall of the tubular perform or formed balloon.

Another way in which the heating may be carried out is by convection using, for example, a hot air gun. For example, the outer surface of a tubular preform or formed balloon may be locally heated by a stream of hot air that locally elevates the temperature of the polymer to or above the melt temperature, thus creating a weakened localized region. Commercially available hot air guns are capable of heating small areas to temperatures of several hundred degrees Celsius.

Preferably, it is possible to focus or localize the heat source to a spot of a few millimeters in diameter in the midsection of the balloon or preform. Preferably, the processing occurs over an area of about 10 $mm^2$ or less as measured on the formed balloon, as described above. It is also preferred that, after the weakening, the localized region has a modified polymer structure relative to other regions of the balloon without having a substantial change in wall thickness.

The weakened localized region may be formed after heating for about 1 minute or less. Preferably, the weakened localized region is formed after heating for about 30 seconds or less.

The weakening of the localized region may include pressurizing a tubular preform of the medical balloon in a heated mold to obtain an inflated portion of the medical balloon, and then weakening a localized region of the inflated portion while the medical balloon is in the mold.

For example, according to one aspect of the method, the preform is inserted into a mold, and the mold is heated to about 100° C. or another temperature suitable for forming the balloon. A first end of the preform is sealed off and a second end is connected to a supply of compressed air or another inflation fluid. The preform is warmed by the mold to a temperature which is preferably below its crystalline melt temperature and then pressurized to produce the inflated portion. A positive pressure in the range of from about 1.5 atm to about 10 atm is generally suitable for pressurizing the preform. An axial force may be applied to one or both ends of the preform during the inflation to stretch the inflated portion and reduce the wall thickness in a controlled manner. Once the balloon has been formed, the inflated portion may be cooled by, for example, flushing with compressed air.

To weaken the localized region of the inflated portion, the localized region may then be heated to a temperature greater that that attained by the preform in the heated mold. For example, the localized region may be heated to a desired temperature at or above the melt temperature of the polymer. In the case of a PET balloon, for example, the desired temperature may be at least about 182° C. (about 360° F.). The heating may be carried out by activating a resistive heating element in the mold adjacent to the localized region of interest.

It is also contemplated that a small region of the balloon's midsection may be may be mechanically processed to form the weakened localized region. For example, a portion of the polymer preform (tubing) from which the balloon is formed may be mechanically abraded. During the forming of the balloon, which is described below, the abraded region may become an area of reduced wall thickness, thereby providing the weakened localized region. It is also contemplated an axial force may be applied to one or both ends of the preform during the forming of the balloon as a means of locally reducing the wall thickness of the balloon.

A medical balloon having a resistance to circumferential tearing has been described. The medical balloon has a midsection including at least one weakened localized region, which is a small portion of the balloon that has a lower resistance to tearing than other portions of the balloon and thus acts as a failure initiation site at high inflation pressures. The inventor has recognized that if a failure occurs in the midsection of the balloon, it tends to propagate longitudinally and substantially dissipate its energy before it reaches one or both ends, where longitudinal tears otherwise tend to change direction and move circumferentially. By engineering the medical balloon to include such a weakened localized region in the midsection, circumferential tears that may result in the balloon's fragmenting into two or more pieces ("radial bursts") can be avoided.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A medical balloon having a resistance to circumferential tearing, the medical balloon comprising:
a substantially cylindrical portion disposed between first and second tapered portions, the first and second tapered portions having a decreasing cross-sectional area along a length thereof away from the cylindrical portion, the substantially cylindrical portion comprising first and second end portions and a midsection disposed therebetween, the midsection spanning no more than about 30% of a total length of the medical balloon and comprising a first region having a first resistance to tearing and one or more second regions having a second resistance to tearing, the second resistance to tearing being lower than the first resistance to tearing and lower than a resistance to tearing of the first and second end portions,
wherein the one or more second regions in total extend less than 10% of a circumference of the substantially cylindrical portion and do not extend beyond the midsection, and wherein the one or more second regions extend through the entire thickness of the medical balloon.

2. The medical balloon of claim 1 wherein the one or more second regions span no more than about 5% of the circumference of the substantially cylindrical portion.

3. The medical balloon of claim 1 wherein the one or more second region comprise a surface area of about 5 mm$^2$ or less.

4. The medical balloon of claim 1 wherein the one or more second regions comprise a wall thickness substantially the same as that of the first region.

5. The medical balloon of claim 1 comprising two or more second regions in the midsection.

6. The medical balloon of claim 1 wherein the one or more second regions span no more than about 5% of the circumference of the substantially cylindrical portion, the one or more second regions comprising a surface area of about 5 mm$^2$ or less and a wall thickness substantially the same as that of the first region.

7. A medical balloon having a resistance to circumferential tearing, the medical balloon comprising a midsection disposed equidistant between first and second ends of the medical balloon and spanning no more than about 30% of a total length between the first and second ends, the midsection comprising a weakened localized region not extending beyond the midsection, wherein the weakened localized region extends through the entire thickness of the medical balloon.

8. The medical balloon of claim 7 wherein the weakened localized region spans no more than about 10% of the total length between the first and second ends.

* * * * *